(12) United States Patent
Babish

(10) Patent No.: US 6,506,420 B2
(45) Date of Patent: Jan. 14, 2003

(54) COMBINATIONS OF PSYLLIUM AND CHITOSAN FOR SYNERGISTIC ADSORPTION OF TRIGLYCERIDE

(75) Inventor: John G. Babish, Brooktondale, NY (US)

(73) Assignee: MetaProteomics, LLC, San Clemente, CA (US)

( * ) Notice: Subject to any disclaimer, the term of this patent is extended or adjusted under 35 U.S.C. 154(b) by 0 days.

(21) Appl. No.: 10/109,954

(22) Filed: Mar. 29, 2002

(65) Prior Publication Data

US 2002/0137729 A1 Sep. 26, 2002

Related U.S. Application Data

(63) Continuation-in-part of application No. 09/621,208, filed on Jul. 21, 2000, now abandoned.

(51) Int. Cl.⁷ .................. A01N 65/00; A61K 35/78; A61K 9/48; A61K 47/00; A23L 1/168
(52) U.S. Cl. .................. 424/738; 424/451; 424/452; 424/464; 424/465
(58) Field of Search ................... 424/725, 738, 424/451, 452, 464, 465; 426/618, 648; 514/55, 783

(56) References Cited

U.S. PATENT DOCUMENTS

| | | | |
|---|---|---|---|
| 4,223,023 A | 9/1980 | Furda | |
| 5,173,296 A | 12/1992 | Andre et al. | |
| 5,258,181 A | 11/1993 | Cregier et al. | |
| 5,380,522 A | 1/1995 | Day | |
| 5,453,282 A | 9/1995 | Kanauchi et al. | |
| 5,773,427 A | 6/1998 | Day | |
| 5,891,441 A | 4/1999 | Diaz et al. | |
| 5,932,561 A | 8/1999 | Meyers et al. | |
| 5,976,550 A | 11/1999 | Engel et al. | |
| 6,048,532 A | 4/2000 | Diaz, et al. | |

OTHER PUBLICATIONS

Computer West Abstract JPAB Aoe et al JP40586227 A Apr. 6, 1993.*

Aoe, Seiichiro et al Water–Soluble Dietary Fiber Complex and Food Composition Containing the Same JPAB Abstract–JP405086227 A Pub Apr. 6, 1993.

* cited by examiner

*Primary Examiner*—Herbert J. Lilling
(74) *Attorney, Agent, or Firm*—Knobbe, Martens, Olson & Bear, LLP

(57) ABSTRACT

A composition and method for minimizing the absorption of triglycerides and fats in the gastrointestinal tract is described. The composition comprises psyllium and chitosan in a ratio range of 2:1 to 11:1 by weight, preferably 2:1 to 9:1, and most preferably 2:1 to 4:1 to provide a synergistic fat-binding effect.

10 Claims, 6 Drawing Sheets

[A]

[B]

COMBINATIONS OF PSYLLIUM AND CHITOSAN FOR SYNERGISTIC ADSORPTION OF TRIGLYCERIDE

REFERENCE TO RELATED APPLICATION

This application is a continuation-in-part of application Ser. No. 09/621,208, filed Jul. 21, 2000 now abandoned.

FIELD OF THE INVENTION

The present invention relates generally to a composition and a method for weight loss, reduction of serum cholesterol, and normalization of insulin response without requiring added caloric restriction. More specifically, the present invention relates to combinations of psyllium and chitosan, in a proper ratio, which synergistically adsorb dietary fats and inhibit their gastrointestinal absorption.

BACKGROUND OF THE INVENTION

In recent years, people have tended to become less physically active and consume food that has a high fat content. Such sedentary life styles and excessive lipid ingestion cause obesity and along with it a variety complications, for instance, heart and circulatory diseases, respiratory disease, diabetes and the like.

It is known that the fat content of foods is a major factor in the problem of obesity. It is also understood that the body tends to store fat for future use rather than utilize it immediately, which leads to weight-gain. Furthermore, it has been shown that there is a connection between the amount of fat stored in the body and the level of serum cholesterol, with a diet high in fat being likely to lead to high serum cholesterol levels. As cholesterol has been implicated as a factor in arteriosclerosis or hardening of the arteries, the risk for heart disease and/or a heart attack is increased when a diet high in fat is followed.

Therefore, a composition along with a safe and easy method of treatment, which facilitates a person's effort to lose weight and to control the accumulation of harmful cholesterol, are needed and will be appreciated. Such a composition or method should preferably be capable of aiding a person in accomplishing these goals without requiring additional caloric restriction or interfering with the taste of food. Ideally, such a product or method, by preventing the body from absorbing the fat in such food once ingested, would permit a person to eat the foods they most like, while not unduly worrying about the amount of fats contained therein. Such a composition would aid the body in the rapid elimination of ingested fats prior to digestion in order to prevent the build-up or accumulation of harmful cholesterol.

It is known that dietary supplementation with psyllium, a water-soluble dietary fiber, can be effective in lowering cholesterol levels. In chemical terms, psyllium extract is a water-soluble mucilage consisting of a highly branched, acidic arabinoxylan. The decrease in cholesterol with psyllium supplementation can be affected with or without any additional dietary changes. See, for example, U.S. Pat. Nos. 6,048,532; 5,891,441; 5,258,181 and 5,173,296, which all are incorporated herein by reference.

Chitosan (FIG. 1A) is a natural, polymeric carbohydrate made through the deaceylation of chitin (FIG. 1B). Currently popular as a dietary supplement, chitosan is capable of binding fat, both triaceylgylcerols (TGs) as well as fatty acids. Based upon in vitro data, it has the potential to assist in weight loss and thereby reduce the incidence of obesity-associated conditions such as cardiovascular disease and type II or non-insulin dependent diabetes.

Chitin, the precursor to chitosan, was first discovered in mushrooms by the French researcher Henri Braconnot in 1811. In the 1920s chitin was also isolated from insects. Chitin is the most abundant natural fiber next to cellulose and is similar to cellulose in many respects. The primary source of chitin today is from the shells of shellfish such as crab and shrimp. The preparation of chitosan was described in 1859. It is made by cooking chitin in alkali, much like the process for making soaps. After alkali treatment, the links of the chitosan polymer are composed of repeating glucosamine units containing a free amino group. These amino groups take on a positive charge at pH values below their pKa. At pH values above the pKa, the molecule loses its charge and becomes neutral. This action sequence is important in the physiologic effects of chitosan in binding neutral, dietary triglycerides.

The ability of chitosan to bind fat has generated great interest in the molecule recently. Like some plant fibers, chitosan is not digestible and therefore has no caloric value. However, unlike neutral plant fibers, chitosan's charged nature gives it the potential ability to bind significantly more fat than any plant fiber. Under physiologic conditions, chitosan can bind an average of four to five times its weight in fat, although in vitro studies demonstrate triglyceride binding of as much as 10 to 100 times its weight.

In recent years, it has been found that chitosan can be used as a dietary supplement for reducing lipid absorption in mammals. See, for example, U.S. Pat. Nos. 4,223,023; 5,453,282; 5,976,550; 5,932,561; 5,773,427 and 5,736,532, which are incorporated herein by reference. While the results of in vitro fat binding studies are impressive, it has not been previously disclosed that chitosan can be used for weight loss without subjecting the individual to a restricted calorie diet. Only laboratory animal studies support the weight loss properties of chitosan. Human clinical studies reported in scientific journals do, however, substantiate a significant reduction in serum LDL cholesterol with the use of chitosan. A significant improvement in the ability of chitosan to bind fat would likely enhance the probability of chitosan effectively reducing body weight in humans and non-laboratory mammals.

There is great need for a composition that would function synergistically to prevent or limit the bioavailability of fat and cholesterol in order to aid in weight-loss, reduce cholesterol levels and control blood glucose. The present invention is designed to satisfy such a need in the art and is believed to represent a significant advance in improving a person's health by the rapid elimination of ingested fat and a reduction in the accumulation of harmful cholesterol levels.

SUMMARY OF THE INVENTION

The present invention provides a composition to cause weight loss in a warm-blooded animal comprising psyllium and chitosan in a specified ratio, which adsorbs fats in the stomach and intestinal tract thereby limiting absorption of ingested fat. Moreover, the present composition also reduces serum cholesterol.

The present invention further provides a method of dietary supplementation to a warm-blooded animal which comprises administering to the animal effective amounts of a composition comprising psyllium and chitosan, in a proper ratio, and continuing such administration of the composition until body weight reduction occurs.

The present invention contemplates treatment of obesity, hypercholesterolemia and type 2 diabetes. The present composition reduces the absorption of fat calories and cholesterol, thereby promoting weight loss and decreasing serum cholesterol levels. A pharmaceutically acceptable carrier may also be used in the present composition and formulation. The formulation can be manufactured as any form known to the skilled artisan, for example as solid capsules, caplets, soft-gels, liquids, bars, or functional foods.

Other features and advantages of the invention will become apparent from the following detailed description, taken in conjunction with the accompanying drawings, which illustrate, by way of example, the features of the invention.

DETAILED DESCRIPTION OF THE INVENTION

Figure 1:
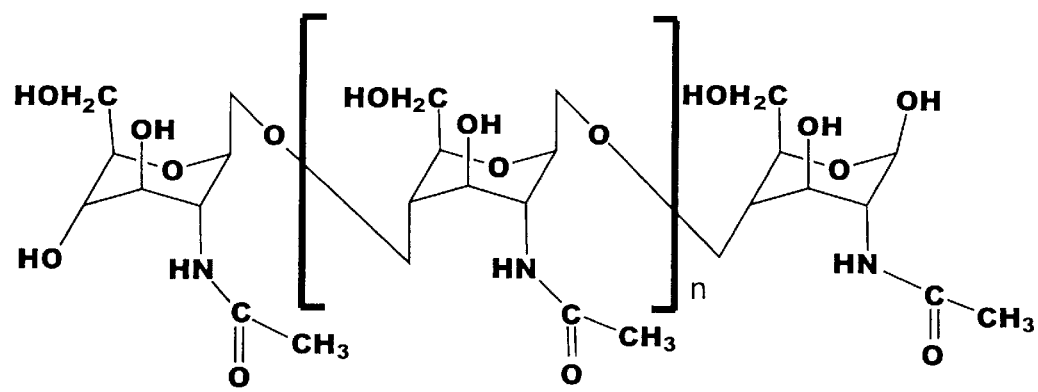
FIG. 1 depicts the chemical structures of [A] chitosan and [B] chitin.
Figure 1:
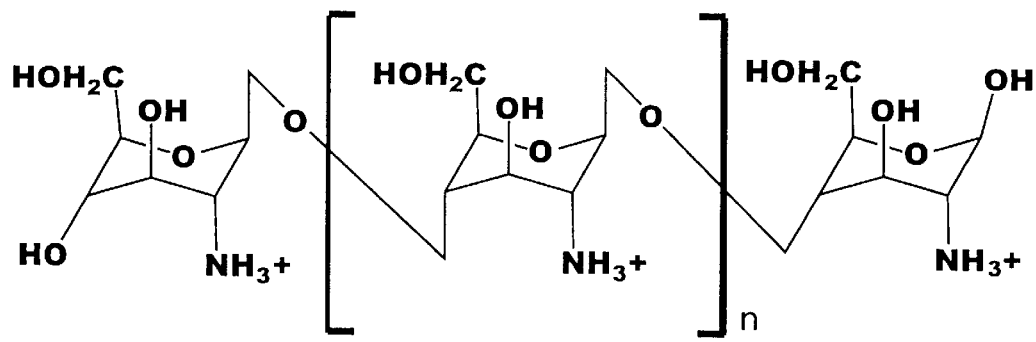

Before the present composition and methods of making and using thereof are disclosed and described, it is to be understood that this invention is not limited to the particular configurations, as process steps and materials may vary somewhat. It is also intended to be understood that the terminology employed herein is used for the purpose of describing particular embodiments only and is not intended to be limiting since the scope of the present invention will be limited only by the appended claims and equivalents thereof. It must be noted that, as used in this specification and the appended claims, the singular forms "a," "an," and "the" include plural referents unless the context clearly dictates otherwise.

The present invention is directed towards a composition and method of use thereof for weight loss, without caloric restriction, in a warm-blooded animal. The composition provided by the present invention can be formulated as a dietary supplement or therapeutic formulation which comprises psyllium and chitosan, in a proper ratio, to provide a synergistic effect on psyllium and chitosan in binding triglycerides and cholesterol and limiting the bioavailability of these dietary components without introducing harmful side effects. Through synergistic reduction of fat and cholesterol absorption, the present composition and method also significantly reduce the risks of cardiovascular diseases, diabetes and respiratory diseases.

It is to be understood, however, that the present invention is not directed to a method or means whereby one can increase caloric intake and still expect to lose weight and/or lower cholesterol levels. Any program directed to the reduction of weight still requires a sensible regimen of caloric intake. Restricting or reducing caloric intake will obviously assist in weight reduction.

The psyllium and chitosan employed in the present invention is a pharmaceutical grade such as that obtained commercially and must pass extensive safety and efficacy procedures. The composition of the present invention comprises psyllium and chitosan with weight ratios within a range of 2:1 to 11:1, preferably in a range of 2:1 to 9:1 and most preferably in a range of 2:1 to 4:1. Preferably, a daily dose (mg/day) of the present formulation would deliver about 500 to 36,000 mg psyllium and about 250 to 4000 mg of chitosan. It is found that the ratios of psyllium to chitosan according to the present invention were perceived as superior and also as having a synergistic effect in binding fat in vitro and eliminating fat from the body following a high fat meal compared to existing fat binding products.

In addition to psyllium and chitosan, the present dietary supplement may include various additives such as other natural components of intermediary metabolism, vitamins, minerals and natural plant products. Examples of natural plant products would include tea, coffee, ephedrine, and phytosterols. Such additions would function to enhance the weight-reducing, cholesterol-lowering and anti-diabetic effect of the formulation. Other inert ingredients such as talc and magnesium stearate that are standard excipients in the manufacture of tablets and capsules would also be obvious to those skilled in the art of pharmaceutical manufacturing.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrates, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in the present composition is contemplated. In one embodiment, talc and magnesium stearate, are included in the present formulation. Other ingredients used to affect the manufacture of this composition, as a dietary bar or functional food, can include flavorings, sugars, aminosugars, proteins and/or modified starches, as well as limited fats and oils.

The dietary supplement or therapeutic composition of the present invention can be formulated in any manner known by one of skill in the art. In one embodiment, the composition is formulated into a capsule or tablet using techniques available to one of skill in the art. However, provided the proper daily dosage is incorporated, the present compositions may also be formulated in other convenient forms, such as a solution or suspension, a spray solution or suspension, a food or snack item. Food, snack, or liquid items can include any ingestible ingredients, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gumdrops, or chewable candies.

Since many modifications, variations and changes in detail can be made to the described preferred embodiment of the invention, it is intended that all matters in the foregoing description and the following examples are interpreted to illustrate and not in any way to limit the invention.

EXAMPLE 1

Adsorption of Triglycerides by Psyllium or Chitosan

This example illustrates the adsorption of fat by psyllium or chitosan in a model system. The amount of triglyceride bound by psyllium or chitosan is measured using a gravimetric procedure and the maximal binding of triglyceride by each fiber is determined under the described model conditions.

A 0.16N HCl solution was made by adding 14 ml of concentrated HCl to 1 liter of distilled water. Reagents A and B were prepared as follows: (1) for Reagent A, 8.48 grams of sodium carbonate was added to 400 ml water and mixed until completely dissolved; (2) for Reagent B, 1.68 grams of sodium bicarbonate was added to 100-ml water and mixed until completely dissolved. Neutralization Buffer was prepared by adding one part of Reagent A to one part of Reagent B.

Two liters each of a 10% psyllium (100% powdered husk, Vitamin World, Ithaca, N.Y.) and a 10% chitosan (LipoSan Ultra, Wilke Resources) suspension were made in the 0.16 N HCl. Shaking was necessary to completely suspend the fibers in the HCl. The suspensions were allowed to set at room temperature for 30 minutes before adding the triglyceride. Commercially available Mazola™ Corn Oil was used as the source of triglyceride in the assay.

One gram of fiber suspended in 10 mL of the 0.16N HCl was added to a 50 mL conical centrifuge tube. For this preliminary study, 20 tubes were used for each fiber. Duplicate sets of ten tubes each were labeled 1 through 10(a) and (b) to represent the amount of triglyceride in g that would be added to the suspended fiber. To each tube was added 1, 2, 3, 4, 5, 6, 7, 8, 9 or 10 grams of triglyceride and the tubes were shaken well. Next, all tubes were placed into a 37° C. water bath for one hour and shaken every 15 minutes. To each tube, 3.5 ml Neutralization Buffer was added and the tubes were then shaken vigorously for 30 seconds. The caps were loosened to allow release of carbon dioxide. The tubes were then centrifuged at 4° C. for 1 hour at 500 rpm in a Forma 5682 Model 120 tabletop, swing-bucket centrifuge. Unbound triglyceride was aspirated from each sample using a 1000 $\mu$L pipette and the weight of the oil removed was recorded. The amount of triglyceride bound was calculated by difference.

Figure 2:
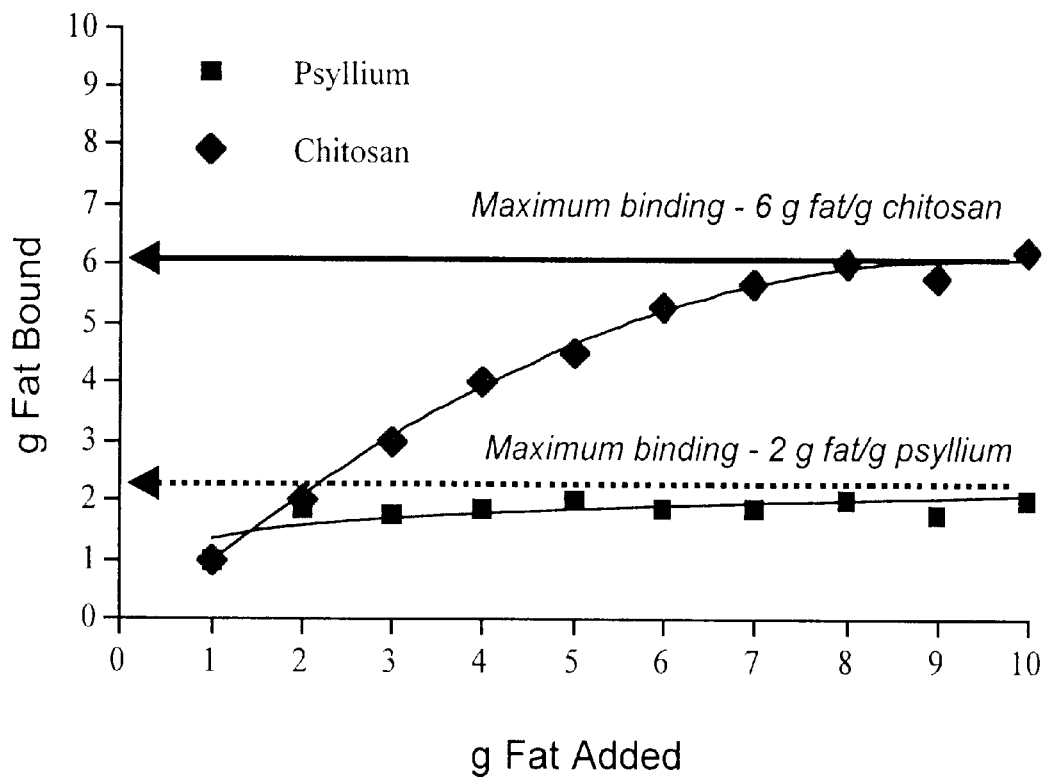
FIG. 2 is a graph of triglyceride binding by psyllium and chitosan in the experiment described in EXAMPLE 1.
Figure 3:
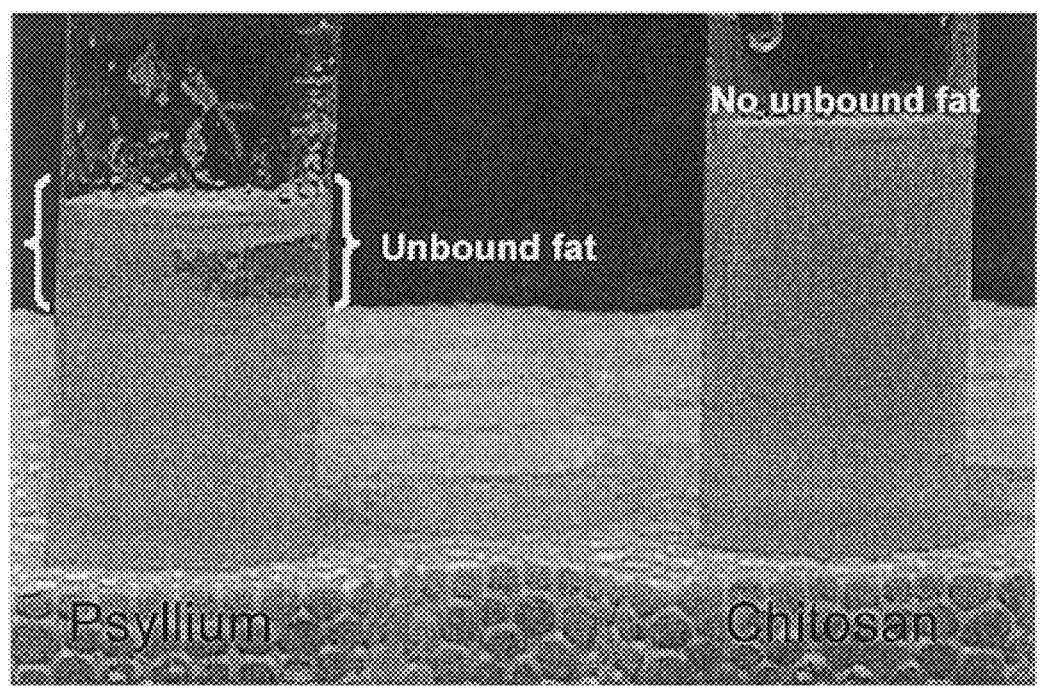
FIG. 3 is a photograph showing the results of fat binding by psyllium and chitosan with the addition of 3 g of triglyceride to the model. The unbound triglyceride is clearly visible as a layer above the psyllium, while an unbound fat layer is not seen for the chitosan.

Both fibers exhibited an ability to bind fat in this model (FIG. 2). At 1 and 2 g fat/g fiber, no differences in fat-binding between the two fibers was seen. However, as the amount of triglyceride added to the system increased to above 2 g fat/g fiber, the differences in fat binding became obvious. The photograph in FIG. 3 depicts the results of fat binding by psyllium and chitosan with the addition of 3 g of triglyceride to the model. The unbound triglyceride is clearly visible as a layer above the psyllium, while an unbound fat layer is not seen for the chitosan. Graphically, the maximal fat binding of each fiber was estimated at 2 g fat/g psyllium and 6 g fat/g chitosan.

The gravimetric fat-binding model described herein demonstrates adsorption of fat by both psyllium and chitosan. Graphically (FIG. 2), both materials exhibit a linear range in the relationship between adsorption of fat and the concentration of fat in the test system. The linear relationship reaches an upper limit for psyllium at 2 g triglyceride/g psyllium and at 6 g triglyceride/g chitosan demonstrating saturation of triglyceride adsorption.

EXAMPLE 2

Adsorption of Triglycerides by Psyllium and Chitosan in the Presence of Excess Psyllium This example illustrates the synergistic adsorption of fat by psyllium and chitosan combinations when the amount of psyllium exceeds chitosan by 2:1 to 11:1.

The procedure for determining fat-binding by psyllium-:chitosan combinations was essentially the same as previously described in EXAMPLE 1. Instead of varying the amount of triglyceride added to the test system, however, a constant 10 g of fat were added to each 1 g of suspension of test fiber combinations. The experimental design is described in Table 1 with expected and actual triglyceride binding results of the test fiber combinations.

TABLE 1

Contrasting expected versus actual fat binding in psyllium:chitosan combinations with psyllium in excess

| Psyllium [g] | Chitosan [g] | Ratio [P:C] | Total Weight [g fiber] | Expected Fat Bound [g fat/g fiber] | Actual Fat Bound [g fat/g fiber] | Actual/Expected** |
|---|---|---|---|---|---|---|
| 1.000 | 0.000 | — | 1.00 | 2.00 | — | — |
| 0.923 | 0.077 | 12 | 1.00 | 2.31 | 2.80 | 1.21 |
| 0.917 | 0.083 | 11 | 1.00 | 2.33 | 3.40 | 1.46 |
| 0.909 | 0.091 | 10 | 1.00 | 2.36 | 3.60 | 1.52 |
| 0.900 | 0.100 | 9 | 1.00 | 2.40 | 3.40 | 1.42 |
| 0.889 | 0.111 | 8 | 1.00 | 2.44 | 3.70 | 1.51 |
| 0.875 | 0.125 | 7 | 1.00 | 2.50 | 4.20 | 1.68 |
| 0.857 | 0.143 | 6 | 1.00 | 2.57 | 4.20 | 1.63 |
| 0.833 | 0.167 | 5 | 1.00 | 2.67 | 4.50 | 1.69 |
| 0.800 | 0.200 | 4 | 1.00 | 2.80 | 4.80 | 1.71 |
| 0.750 | 0.250 | 3 | 1.00 | 3.00 | 4.60 | 1.53 |
| 0.667 | 0.333 | 2 | 1.00 | 3.33 | 4.44 | 1.33 |
| 0.500 | 0.500 | 1 | 1.00 | 4.00 | 4.15 | 1.04 |

*Using the relationship estimated from EXAMPLE 1. FAT BOUND = 2(g psyllium) + 6*(g chitosan) at 10 g fat and 1 gram total fiber.
**Values greater than 1.30 indicate synergy.

Figure 4:
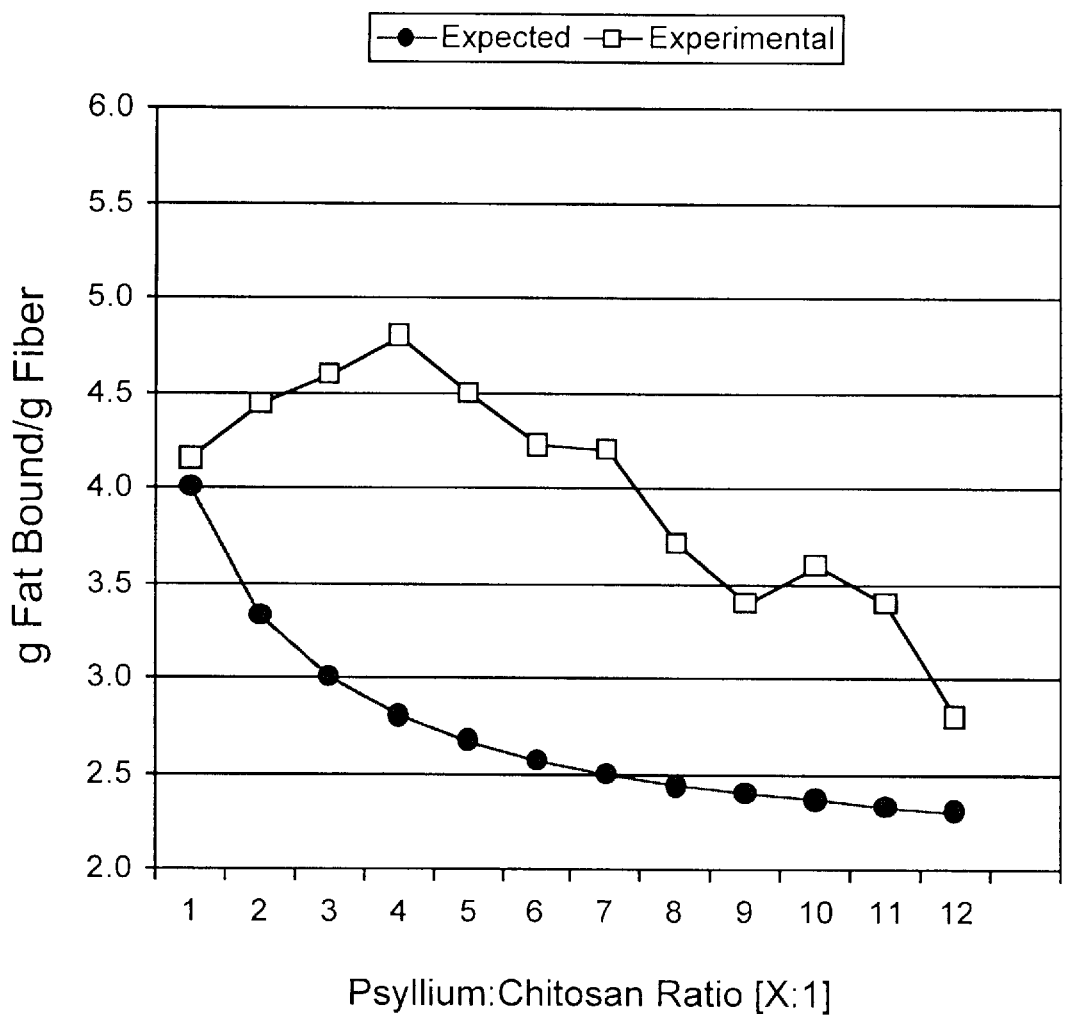
FIG. 4 illustrates the synergistic adsorption of fat by psyllium and chitosan combinations when the amount of psyllium exceeds chitosan by 2:1 to 11:1.

As can be seen in Table 1 and FIG. 4, all test combinations of psyllium and chitosan in which the amount of psyllium exceeded the amount of chitosan bound more triglyceride than what would have been expected from mathematically combining the independent contributions of each fiber. The degree to which the excess binding of triglycerides occurred was an unexpected and novel finding. Combinations of psyllium:chitosan in the range of 2:1 to 11:1 bound over 30 percent more than would be assumed. Deviations from expected values in excess of 20% are generally termed synergistic, as they exceed the confidence limits of extrapolation.

EXAMPLE 3

Adsorption of Triglycerides by Psyllium and Chitosan in the Presence of Excess Chitosan This example illustrates the lack of synergy for adsorption of fat by psyllium and chitosan combinations when the amount of chitosan in the combinations exceeds that of psyllium.

The procedure for determining fat-binding by chitosan:psyllium combinations was the same as previously described in EXAMPLE 2. The experimental design is described in Table 2 with expected and actual triglyceride binding results of the test fiber combinations.

consisting of 4 parts psyllium (Vitamin World, Ithaca, N.Y.) and 1 part chitosan (ChitoClear™). The six grams of the fiber combination were mixed in 240 ml of orange juice and consumed within two minutes of mixing. Ten minutes later, the subjects consumed a high fat lunch consisting of melted cheese and fried chicken wrapped in a baked pastry shell. As eaten, the shell was dipped in a blue cheese dressing. The approximate weight of the lunch was 650 grams. During the following four-hour observation period, all subjects reported a feeling of "overeating" from the lunch. No other adverse side effects were reported. Within 24 hours, all four subjects reported having one or more bowel movements that contained notable, white marbling in large, well-formed stools presumptive of the presence of fat. This indicates the compositions of the present invention promote rapid expulsion of dietary fat and, therefore, decreases fat absorption.

EXAMPLE 5

Effects of a Psyllium-Chitosan Combination on Body Weight

One of the female subjects from EXAMPLE 4 continued to consume six grams of the psyllium:chitosan mixture utilized in EXAMPLE 4 for 28 days 10 to 30 minutes prior to lunch and dinner. Eating and exercise habits were unaltered. The subject reported daily bowel movements similar to those described by the subjects in EXAMPLE 4 and had

TABLE 2

Contracting expected versus actual fat binding in psyllium:chitosan combinations with chitosan in excess

| Chitosan [g] | Psyllium [g] | Ratio [C:P] | Total Weight [g] | Estimated Fat Bound* [g] | Actual Fat Bound [g fat/g fiber] | Actual/Expected** |
|---|---|---|---|---|---|---|
| 1.000 | 0.000 | — | 1.00 | 6.00 | — | — |
| 0.923 | 0.077 | 12 | 1.00 | 5.69 | 5.50 | 0.97 |
| 0.917 | 0.083 | 1 | 1.00 | 5.67 | 5.80 | 1.02 |
| 0.909 | 0.091 | 10 | 100 | 564 | 5.92 | 1.05 |
| 0.900 | 0.100 | 9 | 1.00 | 5.60 | 5.47 | 0.98 |
| 0.889 | 0.111 | 8 | 1.00 | 5.56 | 5.19 | 0.93 |
| 0.875 | 0.125 | 7 | 1.00 | 5.50 | 5.75 | 1.05 |
| 0.857 | 0.143 | 6 | 1.00 | 5.43 | 5.45 | 1.00 |
| 0.833 | 0.167 | 5 | 1.00 | 5.33 | 5.44 | 1.02 |
| 0.800 | 0.200 | 4 | 1.00 | 5.20 | 4.90 | 0.94 |
| 0.750 | 0.250 | 3 | 1.00 | 5.00 | 4.84 | 0.97 |
| 0.667 | 0.333 | 2 | 1.00 | 4.67 | 4.93 | 1.06 |
| 0.500 | 0.500 | 1 | 1.00 | 4.00 | 3.72 | 0.93 |

*Using the relationship estimated from EXAMPLE 1, FAT BOUND = 2(g psyllium) + 6*(g chitosan) at 10 g fat and 1 gram total fiber.
**Values greater than 1.30 indicate synergy.

Figure 5:
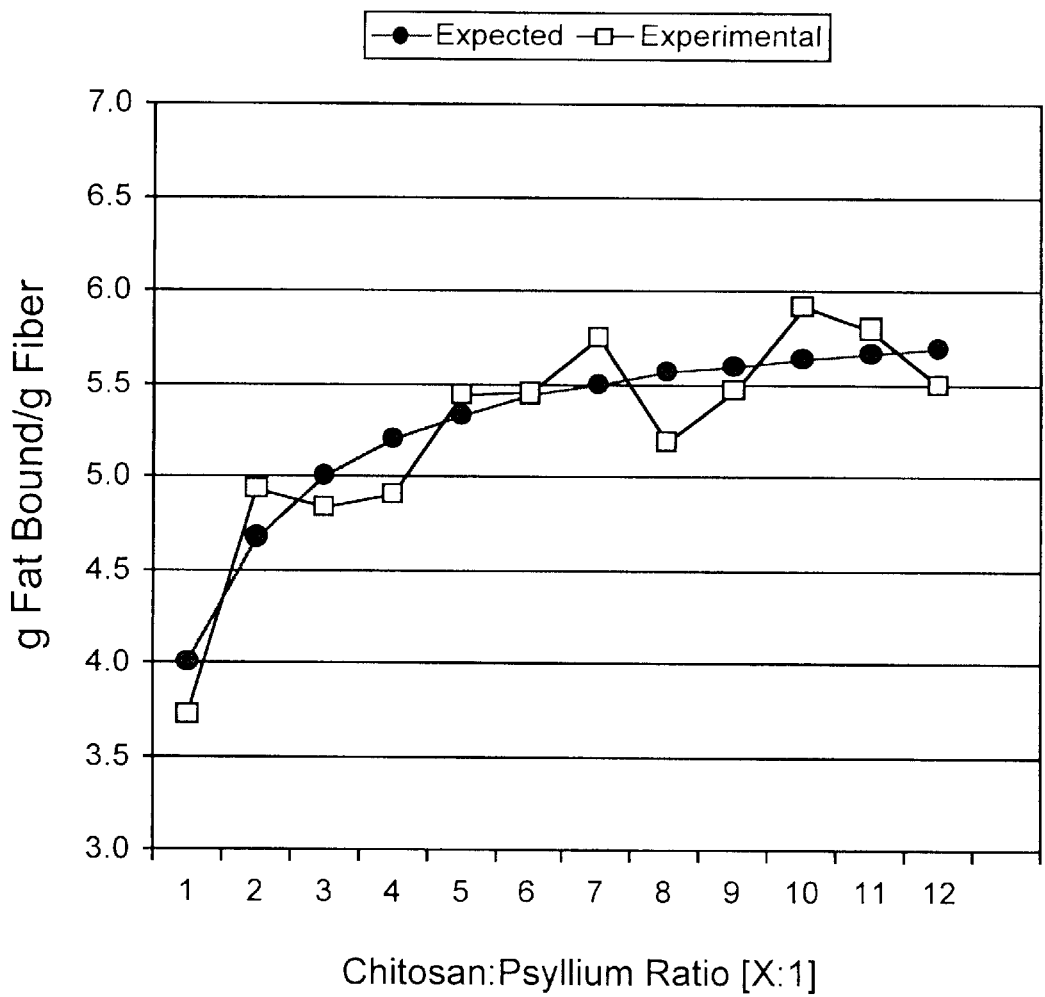
FIG. 5 illustrates the lack of synergy for adsorption of fat by psyllium and chitosan combinations when the amount of chitosan in the combinations exceeds that of psyllium.

As can be seen in Table 2 and FIG. 5, all test combinations of psyllium and chitosan in which the amount of chitosan exceeded the amount of psyllium bound the amount of triglyceride that would have been expected from mathematically combining the independent contributions of each fiber. None of the deviations of experimental values from predicted values exceeded 10%. Therefore, no synergy in triglyceride binding could be inferred for combinations of chitosan and psyllium in which the relative amount of chitosan is equal to or greater than psyllium.

EXAMPLE 4

Effects of a Psyllium-Chitosan Combination on Stool Formation and Appearance

Four adult subjects (three females and one male, with ages ranging from 32 to 53 years) consumed a fiber formulation an unexpected weight loss of 5.45 kg. Prior to the beginning treatment using the psyllium:chitosan combination, this subject experienced frequent bloating and constipation resulting in irregular bowel movements of once every two or three days.

EXAMPLE 6

Effects of a Psyllium-Chitosan Combination on Serum Cholesterol

Figure 6:
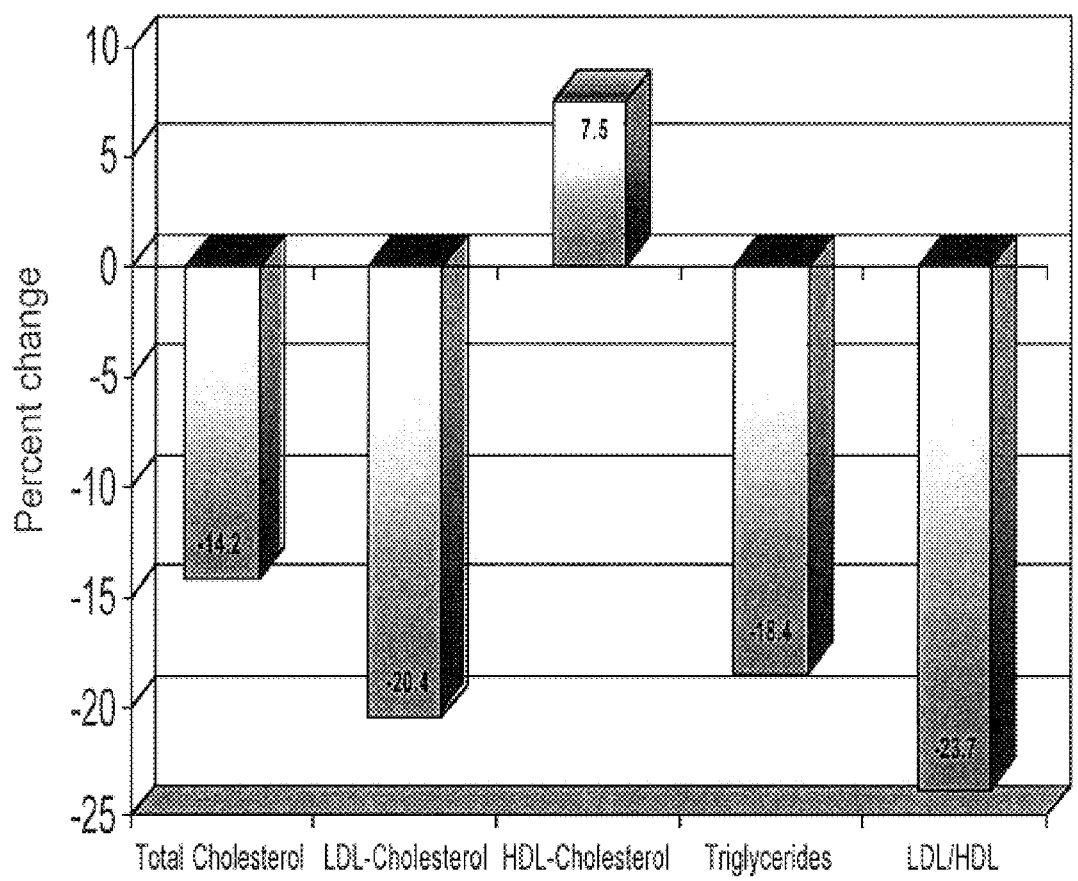
FIG. 6 depicts the changes in serum lipids of a single, female subject who consumed six grams of a psyllium:chitosan (4:1) mixture for 28 days 10 to 30 minutes prior to lunch and dinner.

The same female subject from EXAMPLE 4 continued to consume six grams of the psyllium:chitosan mixture utilized in EXAMPLE 4 for 28 days 10 to 30 minutes prior to lunch and dinner. Eating and exercise habits were unaltered. The subject had undergone a physical examination a week prior to beginning the test regimen. Included in the physical examination was a serum lipid profile consisting of total cholesterol, LDL cholesterol, HDL cholesterol and triglycerides. On day 28 of the study, the subject had the same serum lipid profile repeated. Unexpectedly, it was found that serum cholesterol had decreased 14.2%, LDL cholesterol 20.4% and triglycerides 18.4%. HDL cholesterol increased 7.5% and the LDL/HDL ratio fell 23.7% (FIG. 6). Such dramatic and unexpected changes in serum lipids have not been previously reported for psyllium or chitosan and are generally only seen with prescription drugs.

The synergistically increased triglyceride binding by combinations of psyllium and chitosan, in a proper ratio, is a surprising and unexpected aspect of the present invention. The synergistically enhanced fat binding of these two agents may exert beneficial effects in processes in which inhibition of fat absorption is desirable such as obesity, hypercholesterolemia and diabetes.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

I claim:

1. A composition for inducing weight loss and lowering cholesterol in a warm blooded animal comprising a combination of psyllium and chitosan in a weight ratio of 2:1 to 11:1, said combination being capable of synergistically binding fats comprising triglycerides and cholesterols and, when administered, promoting reduction of the absorption of the fats.

2. The composition of claim 1 wherein said psyllium to chitosan weight ratio is 2:1: to 9:1.

3. The composition of claim 1 wherein said psyllium to chitosan weight ratio is 2:1: to 4:1.

4. The composition of claim 1 further comprises one or more members selected from the group consisting of antioxidants, vitamins, minerals and proteins.

5. The composition of claim 1 further comprises one or more members selected from the group consisting of fats, carbohydrates and natural plant products.

6. The composition of claim 1 is present in a dosage form selected from the group consisting a capsules, tablets, food bars, food supplements, cereals, dairy products and snacks.

7. A method for treating obesity in a warm-blooded animal comprising administering to the animal a composition of claim 1 for a period of time and in an amount sufficient to reduce the symptoms of obesity.

8. The method of claim 7 wherein the composition is administered within said ratios in a daily dosage of 500 to 36,000 mg psyllium and 250 to 4000 mg of chitosan.

9. A method for reducing the serum cholesterol concentration in a warm-blooded animal comprising administering to the animal a composition of claim 1 for a period of time and in an amount sufficient to reduce serum cholesterol concentration of said warm-blooded animal.

10. The method of claim 9 wherein the composition is administered within said ratios in a daily dosage of 500 to 36,000 mg psyllium and 250 to 4000 mg of chitosan.

* * * * *